(12) United States Patent
West

(10) Patent No.: US 6,929,920 B1
(45) Date of Patent: Aug. 16, 2005

(54) DIAGNOSIS OF CHRONIC OBSTRUCTIVE PULMONARY DISEASE

(75) Inventor: Michael Robert West, Buntingford (GB)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 09/980,070

(22) PCT Filed: May 25, 2000

(86) PCT No.: PCT/GB00/02015

§ 371 (c)(1),
(2), (4) Date: Feb. 27, 2002

(87) PCT Pub. No.: WO00/73803

PCT Pub. Date: Dec. 7, 2000

(30) Foreign Application Priority Data

May 29, 1999 (GB) .............................................. 9912534

(51) Int. Cl.[7] ........................ G01N 33/53; G01N 33/574
(52) U.S. Cl. ...................... 435/7.1; 435/7.23; 435/810; 435/7.24; 436/15; 436/86; 436/64
(58) Field of Search ................................ 435/7.1, 7.23, 435/810, 7.24; 436/15, 86, 64

(56) References Cited

U.S. PATENT DOCUMENTS

| 5,597,725 A | 1/1997 | Suzuki ........................ 435/328 |
| 5,895,748 A | 4/1999 | Johnson et al. | |

FOREIGN PATENT DOCUMENTS

| EP | 0 826 774 A2 | 4/1998 | |
| JP | 06324046 | 11/1994 | |
| JP | 10-174590 | 6/1998 | |
| WO | 99/53926 | 10/1999 | .......... A61K/31/58 |

OTHER PUBLICATIONS

Bullock et al. Expression of E–Cadherin and alpha, beta and gamma catenin is associated with epithelial shedding in human lung and nose J. Allergy and Clinical Immunology (1998) 101: S111.*

Kataymata et al. Soluble Fragments of E–Cadherin cell adhesion molecule increase in urinary excretion of cancer patients, potentially indicating its shedding from epithelial tumor cells. International J. Oncology (1994) 5: 1049–1057 (Abstract).*

Cioffi et al Serum–soluble E–cadherin fragments in lung cancer Tumorl (1999) 85: 32–34 (Abstract).*

Loveridge et al., American Review of Respiratory Disease, vol. 134 (5), pp. 930–934 (1986).

Banks et al., Journal of Clinical Pathology, vol. 48, pp. 179–180 (1995).

Pittard, et al., British Journal of Anaesthesia, vol 76, pp. 629–631 (1996).

Maguire, et al., European Journal of Cancer, vol. 33, pp. 404–408 (1997).

Griffiths, et al., "Cell adhesion molecules in bladder cancer: soluble serum E–cadherin correlates with predictors of recurrence," *British Journal of Cancer*, 74: 579–584 (1996).

Pasdar, et al., "Inhibition of Junction Assembly in Cultured Epithelial Cells by Hepatocyte Growth Factor/Scatter Factor is Concomitant with Increased Stability and Altered Phosphorylation of the Soluble Junctional Molecules," *Cell Growth & Differentiation*, 8: 451–462 (1997).

Damsky, et al., "Identification and Purificationof a Cell Surface Gylcoprotein Mediating Intercelular Adhesion in Embryonic and Adult Tissue," *Cell*, 34: 455–466 (1983).

Matsuyoshi, et al., "Soluble E–Cadherin: a novel cutaneous disease marker," *British Journal of Dermatology*, 132: 745–749 (1995).

Berglert, et al., "Protein EnvM is the NADH–dependent Enoyl–ACP Reductase (FabI) of *Escherichia coli*", The Journal of Biological Chemistry, 269(8): 5493–5496 (1994).

* cited by examiner

Primary Examiner—Long V. Le
Assistant Examiner—Jacob Cheu
(74) *Attorney, Agent, or Firm*—Jason C. Fedon; Edward R. Gimmi; Charles M. Kinzig

(57) ABSTRACT

Methods of determining Chronic Obstructive Pulmonary Disease (COPD) severity in patients which comprises measuring the concentration of soluble E-cadherin (sE-cadherin) in the patient's urine and/or blood serum and determining the extent of severity by reference to correlation graphs, a method of treating patients with COPD, methods for determining the responsiveness of said patients to said treatment and a prognostic product for detecting the concentration of sE-cadherin in urine and/or blood serum.

7 Claims, 2 Drawing Sheets

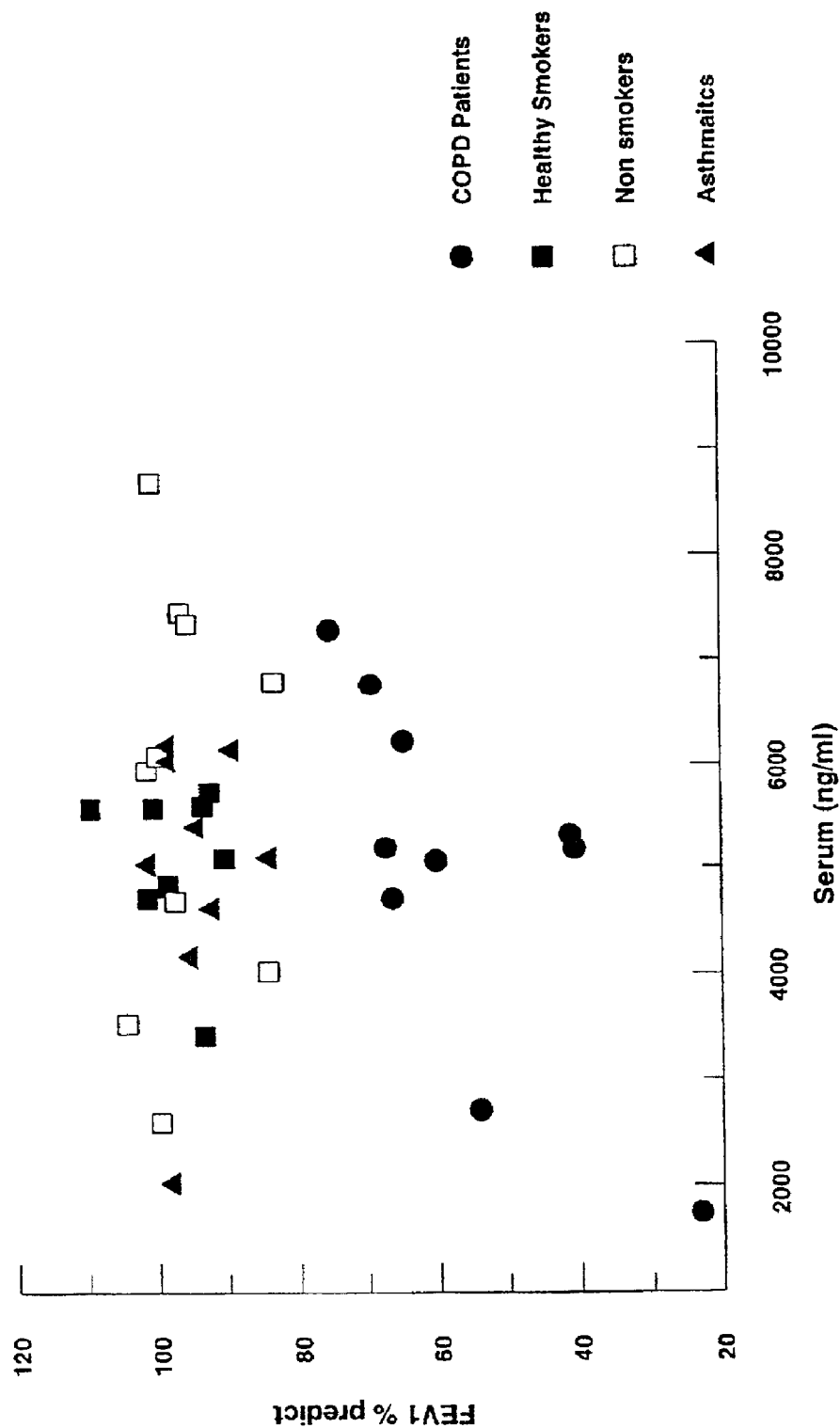

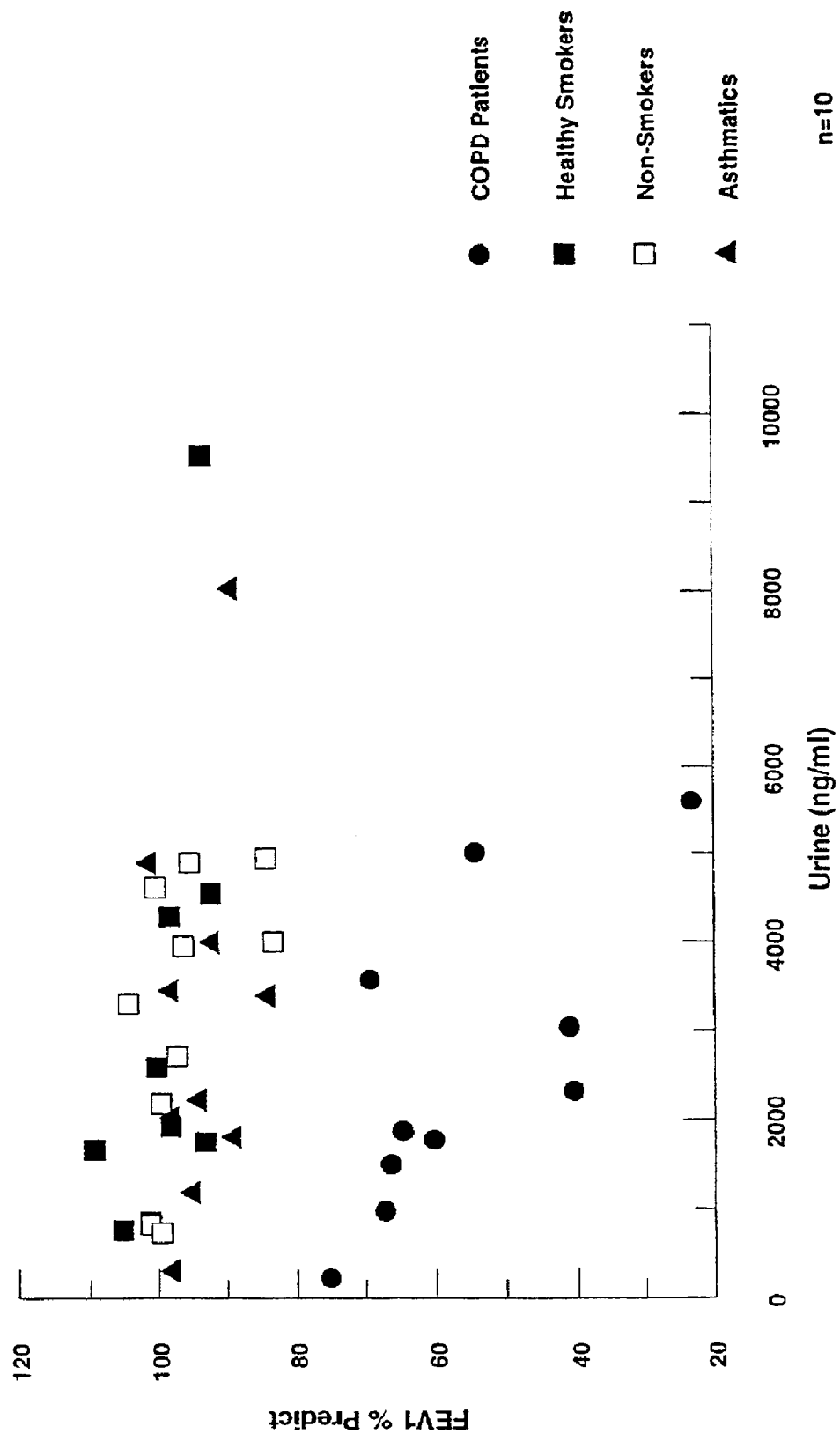

DIAGNOSIS OF CHRONIC OBSTRUCTIVE PULMONARY DISEASE

This invention relates to a novel method for prognosis of a patient with a respiratory disease, specifically chronic obstructive pulmonary disease.

Chronic obstructive pulmonary disease (COPD) is a disease characterised by chronic inflammation and irreversible airflow obstruction with a decline in the lung function parameter FEV1 that is more rapid than normal. The disease has two major aspects of pathology, namely chronic bronchitis, characterised by mucus hypersecretion from the conducting airways, and emphysema, characterised by destructive changes in the alveoli.

Currently a number of pharmaceutical substances are indicated for or have been shown to be useful in treating the symptoms of COPD, including salmeterol xinafoate, fluticasone propionate and ipratropium bromide. (2R,3R,4S,5R)-2-[6 Amino-2-(1S-hydroxymethyl-2-phenyl-ethylamino)-purin-9yl]5-(2-ethyl-2H-tetrazol-5yl)-tetrahydro-furan-3,4-diol is also of development interest in the treatment of COPD, as are tiotropium, 4hydroxy-7-[2-[[2-[[3-(2-phenylethyoxy)propyl]sulfonyl]ethyl]amino]ethyl2(3H)-benzothiazolone and cis-20 4cyano4-[3-(cyclopentyloxy)4methoxyphenyl]cyclohexanecarboxylic acid. However there is considerable interest in evaluating the extent, if at all, these medicines are disease modifying i.e. affect the overall progression of the disease either in terms of symptom severity or exacerbation severity.

Additionally many of the symptoms of COPD are shared by other respiratory diseases such as asthma, bronchitis, pulmonary fibrosis and tuberculosis. Accordingly COPD is considered to be a poorly diagnosed disease and due to this fact a great number of patients are denied medicine that could be of benefit to them. In addition, there is a need for new medicines that will be more effective than current medicines. In view of the economic impact of COPD there is considerable incentive for drug discovery in this area.

The presenting symptoms for COPD are breathlessness accompanied by a decline in FEV1. Chronic bronchitis can be diagnosed by asking the patient whether they have a "productive cough" i.e. one that yields sputum. Patients are traditionally treated with bronchodilators or steroids and examined by spirometry for reversibility of airflow obstruction. If reversibility is less than 15%, and particularly if they have a long history of smoking, then they would be classified as COPD patients.

The ATS (American Thoracic Society) criteria for diagnosing COPD are as follows:
FEV1/FVC ratio<0.7
FEV1<70% predicted, <15% reversibility to inhaled B2 agonist
PLUS:
2 week oral prednisolone trial—less than 15% reversibility in FEV1
Smoking history
Excluding alpha-1 AT deficiency (by blood test)
Non-atopic (skin tests) and no history of atopy
Stable: without exacerbation for at least 6 weeks
No history of childhood asthma There is a need in the art to identify a reliable and straightforward indicator of the COPD disease state (for example, a surrogate marker) both in order to reliably distinguish the symptoms of COPD from those of the above mentioned respiratory diseases and to predict changes in disease severity and progression, and response to medicine, before these changes are manifest clinically.

Elevated levels of cytokeratin 19 fragments have been detected in the broncheoalveolar lavage fluid of patients with chronic inflammatory lung disease and this observation was suggested as a marker of bronchial epithelial injury (Nakamura, H. et al., 1997: Am. J. Resp. Crnt. Care Med. 155, 1217–1221). However, no attempt was made to correlate levels of this marker with lung function (e.g. FEV1). The inventors of the present invention have surprisingly identified a hitherto unappreciated correlation between the concentration of soluble E-cadherin in blood serum and urine in a patient and the severity of COPD as measured by a reduction in the patient's FEV1.

FEV1 is the volume of air expelled from the lungs in one second, starting from a position of maximum inspiration and with the subject making maximum effort. FEV1% is the FEV1 expressed as a percentage of the forced vital capacity (FVC). The FVC is the total volume of air expelled from the lungs from a position of maximum inspiration with the subject making maximum effort.

FEV1 may be measured using a spirometer to measure the volume of air expired in the first second of exhalation.

E-cadherin is a member of the calcium dependent adhesion molecule superfamily and is expressed in epithelia, including those of the lung, gut and skin. It has a major role in controlling epithelial intercellular adhesion since it influences the formation of all epithelial intercellular junctions. Adhesion is mediated by interaction between extracellular domains of E-cadherin dimers on adjacent cells. In the adherens junction, cadherin dimers assemble in a zipper-like manner increasing the adhesive strength. In certain epithelial hyperproliferative conditions, there is some shedding of E-cadherin extracellular domains as soluble fragments, (sE-cadherin). The concentration of sE-cadherin in the circulation has been shown to be increased in patients with certain turmours and also to correlate with the PASI score (measure of disease severity) of psoriasis patients (Matsuyoshi, N. et al. (1995) Brit. J. Dermatol. 132, 745–749).

Concentration of E-cadherin in the blood serum or urine may be determined using a specific ELISAl Using this assay, the inventors have shown a direct and inverse linear correlation between actual FEV1 in COPD patients (as a percentage of the predicted value of FEV1) and sE-cadherin levels in serum and urine respectively.

The results of a trial demonstrating these correlations are described in Example 1 and shown in FIGS. 1 and 2.

Thus the concentration of soluble E-cadherin in blood serum and urine is a molecular indicator for COPD which is capable of reporting its severity without recourse to evaluating any symptom except reduction in a patient's FEV1.

The predicted (normal) FEV1 of a patient may be calculated by the methods determined by Morris JF et al 1971: Am Rev Resp Dis 103, 57–67 based on given height and age. The values are influenced by age, sex and height.

A patient already diagnosed as having COPD can be assayed for disease severity at a time point by comparison of his concentration of soluble E-cadherin in blood serum or urine at that time point with the indicator of severity shown in FIGS. 1 and 2.

Progression of COPD disease may be evaluated by monitoring the concentration of soluble E-cadherin in blood serum or urine with time.

It will be appreciated that either the concentration of soluble E-cadherin in blood serum or urine may be measured for the prognosis, however the recordal of both measurements will be confirmatory of the prognosis. The strength of the confirmation is emphasised by the inverse correlation between the two measurements as shown in FIGS. 1 and 2.

It will be appreciated that a particular and unique benefit of the invention is the ease of prognosis which may be performed requiring only a simple blood or urine sample.

Thus, according to the invention, we provide a method of determining the severity of COPD in a patient which comprises measuring the concentration of soluble E-cadherin in a sample of the patient's urine and determining the extent of severity by reference to a correlation graph such as one which correlates FEV1 (as a percentage of the predicted value) with soluble E-cadherin concentration eg. as shown in FIG. 2.

We also provide a method of determining the severity of COPD in a patient which comprises measuring the concentration of soluble E-cadherin in a sample of the patient's blood serum and determining the extent of severity by reference to a correlation graph such as one which correlates FEV1 (as a percentage of the predicted value) with soluble E-cadherin concentration eg. as shown in FIG. 1.

For greater confidence, the method may comprise measuring the concentration of soluble E-cadherin in a sample of the patient's blood serum and urine and determining the extent of severity by reference to a correlation graph for each such as one which correlates FEV1 (as a percentage of the predicted value) with soluble E-cadherin concentration eg. as shown in FIGS. 1 and 2.

As a further aspect of the present invention we provide a method of treating a patient suffering from COPD which comprises determining the extent of the disease by identifying the levels of soluble E-cadherin in a sample of the patient's blood serum followed by administration of a compound which ameliorates the symptoms of the disease.

We also provide a method of treating a patient suffering from COPD which comprises determining the extent of the disease by identifying the levels of soluble E-cadherin in a sample of the patients urine followed by administration of a compound which ameliorates the symptoms of the disease.

We also provide a method of treating a patient suffering from COPD which comprises determining the extent of the disease by identifying the levels of soluble E-cadherin in a sample of the patient's blood serum and urine followed by administration of a compound which ameliorates the symptoms of the disease.

As a further aspect of the invention we provide a method of determining the responsiveness of a patient with COPD to therapy which comprises monitoring the concentration of soluble E-cadherin in samples of the patient's blood serum with time and determining the rate of change of extent of progression of the disease by reference to a correlation graph such as one which correlates FEV1 (as a percentage of the predicted value) with soluble E-cadherin concentration eg. as shown in FIG. 1.

We also provide a method of determining the responsiveness of a patient with COPD to therapy which comprises monitoring the concentration of soluble E-cadherin in samples of the patient's urine with time and determining the rate of change of extent of progression of the disease by reference to a correlation graph such as one which correlates FEV1 (as a percentage of the predicted value) with soluble E-cadherin concentration eg. as shown in FIG. 2.

For greater confidence, the method may comprise monitoring the concentration of soluble E-cadherin in samples of the patient's urine and blood serum with time and determining the rate of change of extent of progression of the disease by reference to a correlation graph for each such as one which correlates FEV1 (as a percentage of the predicted value) with soluble E-cadherin concentration eg. as shown in FIGS. 1 and 2.

As a further aspect of the invention we provide a product for prognosis of COPD severity in a patient which comprises means to report the concentration of soluble E-cadherin in a sample of blood serum taken from the patient.

We also provide a product for the prognosis of COPD severity in a patient which comprises means to report the concentration of soluble E-cadherin in a sample of urine taken from the patient.

We also provide use of means to report the concentration of soluble E-cadherin in a sample of a patient's urine in the manufacture of a prognostic product for determination of COPD disease severity in a patient.

We also provide use of means to report the concentration of soluble E-cadherin in a sample of a patient's blood serum in the manufacture of a prognostic product for determination of COPD disease severity in a patient.

For blood serum analysis, a 20–30 $\mu l$ volume of blood taken from a 'pin-prick' would be suitable and for urine analysis a sample of approximately 1 ml taken "mid-flow" would be suitable.

Means to report the concentration of soluble E-cadherin in a sample of blood serum or urine preferably comprises an anti-soluble E-cadherin antibody.

For example, sE-cadherin concentration may be measured using a commercially available kit from Takara. This kit allows the measurement of sE-cadherin, using standard ELISA technology and the standard curve provided, which allows interpretation of the measurement in terms of a concentration.

EXAMPLE 1

Blood serum, urine and induced sputum from 4 patient groups (healthy non-smokers, healthy smokers, asthmatics and COPD patients) were sampled and the soluble E-cadherin concentration in each body fluid was measured.

FEV1 was measured using the method given above. Predicted (normal) FEV1 was calculated for each patient in accordance with the algorithm given in the above mentioned Morris et al (1971) paper and the actual FEV1 given as a percentage of predicted.

Table 1 contains information relating to all patients used in this example.

Pack years refers to the level of smoke exposure. One pack year equates to 20 cigarettes smoked per day for 1 year. The medicaments used in the table refer to 'salb': salbutamol and 'atro': Atrovent (ipratropium bromide).

The results are shown in the following Figures:

FIG. 1—FEV1 (as a percentage of the predicted value) as a function of concentration of soluble E-cadherin in blood serum FIG. 2—FEV1 (as a percentage of the predicted value) as a function of concentration of soluble E-cadherin in urine.

The predicted value of FEV1 was determined according to Morris JF et al 1971: Am Rev Resp Dis 103, 57–67.

The results presented in FIG. 1 show that FEV1 (as a percentage of the predicted value) (y) is correlated with concentration of soluble E-cadherin in blood serum (x) in COPD patients according to Spearman's rank correlation analysis.

The correlation coefficient and p-values for the 4 patient groups from these data are as follows:

|  | Corr coeff | p-value |
|---|---|---|
| Healthy non-smokers | −0.36 | 0.521 |
| Healthy smokers | −0.23 | 0.307 |
| Asthmatics | 0.02 | 0.946 |
| COPD patients | 0.67 | 0.033 |

The results presented in FIG. 2 show that FEV1 (as a percentage of the predicted value) (y) is correlated with concentration of soluble E-adherin in urine (x) in COPD patients according to Speannan's rank correlation analysis.

The correlation coefficient and p-values for the 4 patient groups from these data are as follows:

|  | Corr. coeff. | p-value |
|---|---|---|
| COPD | −0.66 | 0.038 |
| Healthy Smokers | −0.76 | 0.016 |
| Healthy Non-Smokers | −0.57 | 0.088 |
| Asthma | −0.11 | 0.761 |

Both FIGS. 1 and 2 show that there is no correlation between FEV1 and concentration of soluble E-cadherin in urine or blood serum in asthmatics.

TABLE 1

| Patient Group | | Mean [sE-cadherin] in sputum supernatant (ng/ml) | Mean [sE-cadherin] in serum (ng/ml) | Mean [sE-cadherin] in urine (ng/ml) | Mean [IL-8] | Mean [Creatinine] (mmol/L) | [Urine]/[Creatinine] ratio | Age of patient | Sex of patient | Medication taken by patient | Pack Years | FEV1 % pred |
|---|---|---|---|---|---|---|---|---|---|---|---|---|
| COPD | 1 | 294 | 5082 | 1795 | 5049 | 8.1 | 222 | 59 | F | nil | 35 | 60 |
| COPD | 2 | 94 | 4728 | 1518 | 10661 | 1.3 | 1168 | 66 | M | salb, atro | 44 | 66.2 |
| COPD | 3 | 810 | 6239 | 1900 | 3218 | 4.7 | 404 | 48 | M | nil | 30 | 64.5 |
| COPD | 4 | 71 | 7297 | 255 | 3598 | 0.6 | 425 | 45 | M | nil | 30 | 75 |
| COPD | 5 | 830 | 5342 | 3066 | 548 | 17.5 | 175 | 47 | M | atro | 25 (ex) | 41 |
| COPD | 6 | 1749 | 6781 | 3603 | 4809 | 12.4 | 291 | 43 | M | nil | 30 | 69 |
| COPD | 7 | 179 | 5208 | 996 | 15397 | 3.2 | 311 | 45 | F | nil | 30 | 67.1 |
| COPD | 8 | 821 | 1761 | 5617 | 14056 | 10.9 | 515 | 54 | M | nil | 40 | 23 |
| COPD | 9 | 815 | 5198 | 2340 | 11147 | 2.8 | 836 | 56 | F | nil | 40 | 40.4 |
| COPD | 10 | 658 | 2736 | 5034 | 2954 | 12.3 | 409 | 65 | M | salb, atro | 30 (ex) | 54 |
| Mean values of Patient Group | | 632 | 5037 | 2612 | 7144 | 7.4 | 476 | 53 | 7 M | — | 35 | 56 |
| Healthy Smokers | 1 | 506 | 5612 | 1775 | 827 | 9.4 | 189 | 42 | F | nil | 15 | 93 |
| Healthy Smokers | 2 | 547 | 5740 | 4568 | 221 | 15 | 304 | 42 | F | nil | 22 | 92 |
| Healthy Smokers | 3 | 376 | 4830 | 4310 | 796 | 17.5 | 246 | 38 | F | nil | 10 | 98 |
| Healthy Smokers | 4 | 463 | 5590 | 2609 | 716 | 4.4 | 593 | 35 | F | nil | 15 | 100 |
| Healthy Smokers | 5 | 446 | 5103 | — | 544 | — | — | 48 | F | nil | 20 | 90 |
| Healthy Smokers | 6 | 837 | 4733 | 878 | 461 | 16 | 55 | 26 | F | nil | 10 | 101 |
| Healthy Smokers | 7 | 1671 | 2761 | 780 | 3362 | 3.5 | 223 | 24 | F | nil | 11 | 105 |
| Healthy Smokers | 8 | 697 | 4856 | 1956 | 673 | 7 | 279 | 33 | F | nil | 15 | 98 |
| Healthy Smokers | 9 | 368 | 5585 | 1684 | 393 | 12.8 | 132 | 28 | M | nil | 10 | 109 |
| Healthy Smokers | 10 | 403 | 3431 | 9558 | 425 | 12.7 | 753 | 38 | F | nil | 20 | 93 |
| Mean values of Patient Group | | 516 | 4824 | 3270 | 562 | 11.4 | 312 | 35 | 1 M | — | 14.8 | 98 |
| Healthy Non-Smokers | 1 | 673 | 5951 | 842 | 704 | 7.4 | 114 | 28 | F | nil | nil | 101 |
| Healthy Non-Smokers | 2 | 1006 | 7463 | 3976 | 179 | 15 | 265 | 41 | F | nil | nil | 96 |
| Healthy Non-Smokers | 3 | 654 | 2617 | 750 | 547 | 3 | 250 | 28 | F | nil | nil | 99.4 |
| Healthy Non-Smokers | 4 | 538 | 4697 | 2737 | 603 | 8 | 342 | 31 | F | nil | nil | 97 |
| Healthy Non-Smokers | 5 | 1118 | 6804 | 4022 | 206 | 17.3 | 232 | 33 | F | nil | nil | 83 |
| Healthy Non-Smokers | 6 | 367 | 3544 | 3329 | 337 | 11.2 | 297 | 21 | F | nil | nil | 104 |
| Healthy Non-Smokers | 7 | 782 | 8697 | 4639 | 667 | 12.4 | 374 | 52 | F | nil | nil | 100 |
| Healthy Non-Smokers | 8 | 673 | 7357 | 4918 | 347 | 11.5 | 428 | 47 | F | nil | nil | 95 |
| Healthy Non-Smokers | 9 | 976 | 4041 | 4963 | 683 | 8.5 | 584 | 43 | F | nil | nil | 84 |
| Healthy Non-Smokers | 10 | 1375 | 6094 | 2199 | 584 | 20 | 110 | 28 | F | nil | nil | 99.4 |
| Mean values of Patient Group | | 816 | 5726 | 3237 | 486 | 11.4 | 300 | 35 | 0 M | — | — | 95.9 |
| Asthma | 1 | 334 | 5041 | 4900 | 753 | 13.7 | 358 | 39 | M | salb | nil | 101 |
| Asthma | 2 | 508 | 2027 | 3464 | 48 | 23 | 151 | 30 | M | salb | nil | 98 |
| Asthma | 3 | 240 | 6153 | 1817 | 73 | 7.1 | 256 | 22 | F | salb | nil | 89 |
| Asthma | 4 | 348 | 4168 | 1190 | 37 | 4.1 | 290 | 41 | F | salb | nil | 95 |
| Asthma | 5 | 577 | 5403 | 2228 | 528 | 10.3 | 216 | 27 | M | salb | nil | 94 |
| Asthma | 6 | 584 | 4625 | 4003 | 539 | 11 | 364 | 27 | M | salb | nil | 92 |
| Asthma | 7 | 320 | 5101 | 3406 | 285 | 16.7 | 204 | 33 | F | salb | nil | 84 |
| Asthma | 8 | 324 | 6190 | 320 | 496 | — | — | 40 | F | salb | nil | 98 |

TABLE 1-continued

| Patient Group | | Mean [sE-cadherin] in sputum supernatant (ng/ml) | Mean [sE-cadherin] in serum (ng/ml) | Mean [sE-cadherin] in urine (ng/ml) | Mean [IL-8] | Mean [Creatinine] (mmol/L) | [Urine]/[Creatinine] ratio | Age of patient | Sex of patient | Medication taken by patient | Pack Years | FEV1 % pred |
|---|---|---|---|---|---|---|---|---|---|---|---|---|
| Asthma | 9 | 1767 | 4044 | 8039 | 2070 | 6.4 | 1256 | 37 | M | salb | nil | 89 |
| Asthma | 10 | 693 | 6038 | 2034 | 125 | 8.5 | 239 | 21 | F | salb | Nil | 98 |
| Mean values of Patient Group | | 436 | 4879 | 3140 | 320 | 11.2 | 370 | 32 | 5 M | — | — | 94 |

What is claimed is:

1. A method of treating a patient suffering from Chronic Obstructive Pulmonary Disease (COPD) which comprises determining the extent of the disease by identifying the levels of soluble E-cadherin (sE-cadherin) in a sample of the patient's blood serum or urine and determining the extent of severity by reference to a correlation graph which correlates Forced Expiratory Volume in the first second of expiration (FEV1) with sE-cadherin concentration followed by administration of a compound which ameliorates the symptoms of the disease.

2. A method according to claim 1, wherein said identifying step comprises identifying the concentration of sE-cadherin in a sample of the patient's blood serum.

3. A method according to claim 1, wherein said identifying step comprises identifying the concentration of sE-cadherin in a sample of the patient's urine.

4. A method according to claim 1, wherein said identifying step comprises identifying the levels of sE-cadherin in a sample of the patient's blood serum and urine.

5. A method according to claim 2 wherein the correlation graph correlates FEV1 (as a percentage of the predicted value) with sE-cadherin concentration.

6. A method according to claim 3 wherein the correlation graph correlates FEV1 (as a percentage of the predicted value) with sE-cadherin concentration.

7. A method according to claim 4 wherein the correlation graph correlates FEV1 (as a percentage of the predicted value) with sE-cadherin concentration.

* * * * *